June 21, 1966 M. L. MEILLAND Plant Pat. 2,646
ROSE PLANT
Filed Aug. 13, 1965
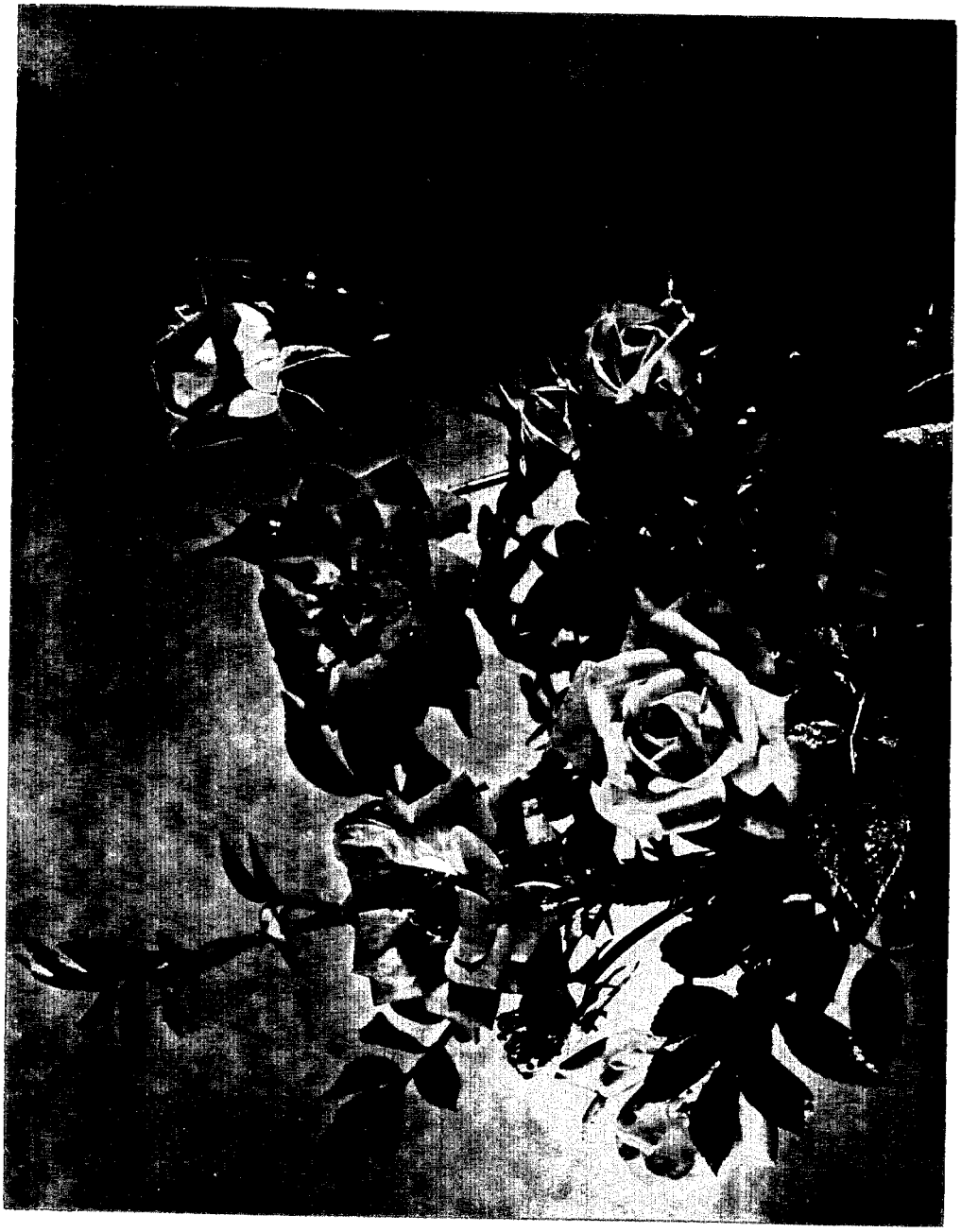
Inventor.
Marie Louise Meilland
By: Robb & Robb
Attorneys.

United States Patent Office

Plant Pat. 2,646
Patented June 21, 1966

2,646
ROSE PLANT

Marie Louise Meilland, Cap d'Antibes, Alpes-Maritimes, France, assignor to The Conard-Pyle Company, West Grove, Pa., a corporation of Pennsylvania Filed Aug. 13, 1965, Ser. No. 479,679
1 Claim. (Cl. Plt.—10)

The present invention relates to a new and distinct variety of rose plant of the miniature class, which was originated by me by crossing an unnamed and unpatented seedling of "Dany Robin" (unpatented) × "Fire King" (U.S. Plant Patent No. 1,758) with the variety known as "Perla de Montserrat" (unpatented).

As the result of this breeding, I have produced a new and improved rose variety which is distinguished from its parents, as well as from all other varieties of which I am aware, as evidenced by the following unique combination of characteristics which are outstanding therein:

(1) A somewhat greater than average plant vigor than that of the average miniature rose variety;
(2) Small flower size, but good flower form;
(3) Good petal count of the double flowers; and
(4) A distinctive and attractive Orange-Scarlet general color tonality of the flowers.

In comparison with its unnamed seedling parent, my new variety has a miniature habit of growth rather than the typical polyantha-floribunda habit of this parent, while the flower color of the new variety is Orange-Scarlet, whereas the flower color of the parent seedling is a bicolor, with Rose-Red on the inside and Amber-White on the reverse side.

As compared with its pollen parent "Perla de Montserrat," the new variety is somewhat more vigorous and its Orange-Scarlet flower color is quite different from the deep red flower color of this parent, which has no orange undertones in its flower color.

Asexular reproduction of the new variety by budding and by cuttings, as performed in France and at West Grove, Pennsylvania, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; dwarf; outdoor; seedling; for garden decoration and for pot forcing.
Class: Miniature.
Breeding: Seedling.
*Seedparent.*—An unnamed seedling of "Dany Robin" × "Fire King."
*Pollen parent.*—"Perla de Montserrat."
Propagation: Holds its distinguishing characteristics through succeeding propagations by budding and by cuttings.

*Flower*

Locality where grown and observed: West Grove, Pennsylvania, U.S.A.
Flowers borne: Usually singly, but sometimes two or three to stem; on stems of normal strength and medium length.

Quantity of bloom: Moderate, both outdoors and in greenhouse.
Continuity: Continuous.
Fragrance: Very slight.
Bud:
*Peduncle.*—Short; slender; erect; almost smooth; few glandular tipped green hairs. Color—Medium Green.
*Before calyx breaks.*—Size—Small. Form—Short; ovoid; with a conspicuous neck; with foliaceous appendages on the surface of the bud; with slender, bristle-like foliaceous parts extending beyond the tip of the bud equal to ¼ or more of its length.
*As calyx breaks.*—Color—Rose Opal, Plate 022, with base of petal Lemon Yellow, Plate 4/2.
*As first petal opens.*—Size—very small. Form—ovoid. Color—Outside: Point of attachment and basal quarter of petal Sulphur Yellow, Plate 1/1, becoming overlaid with Spanish Orange, Plate 010/1, and with remainder of petal Delft Rose, Plate 020/1. Inside: Point of attachment Sulphur Yellow, Plate 1, becoming Delft Rose, Plate 020 over remainder of petal.
*Opening.*—Opens up well.
Bloom:
*Size (when fully open).*—Small; from 1½ inches to 1¾ inches, but occasionally larger.
*Petalage.*—Double; from 23 to 28 petals; arranged regularly.
*Form.*—High-centered at first, but becoming flat; petals being at first loosely rolled outward and remaining loosely rolled outward at maturity.
Petals:
*Texture.*—Medium thickness. Inside—satiny. Outside—satiny.
*Shape.*—Outer petals—obovate. Intermediate petals—obovate. Inner petals—obovate.

This description of a newly opened flower was made from a rose grown in a greenhouse during the month of September at West Grove, Pennsylvania, U.S.A.:

*Color.*—Outer petal: Outside surface—outer half of petal Spinel Red, Plate 0023/1, becoming underlaid with Mimosa Yellow, Plate 602/2, then changing abruptly to Mimosa Yellow, Plate 602/1 over lower quarter of petal. Inside surface—outer half of petal Delft Rose, Plate 020, becoming Jasper Red, Plate 018, with basal quarter of petal Mimosa Yellow, Plate 602. Intermediate petal: Outside surface—Rhodonite Red, Plate 0022, forming a broad margin around the outer edge of the upper half of the petal, becoming underlaid with Mimosa Yellow, Plate 602/1, and with basal quarter of petal Mimosa Yellow, Plate 602/1. Inside surface—outer half of petal between Geranium Lake, Plate 20 and Plate 20/1, with basal quarter of petal Mimosa Yellow, Plate 602/1. Inner petal: Outside surface—Spinel Red, Plate 0023, covering upper ⅓ of petal, becoming underlaid with Mimosa Yellow, Plate 602/1, and with basal quarter of petal Mimosa Yellow, Plate 602/1. Inside surface—upper half of petal Geranium Lake, Plate 20, changing to Vermillion, Plate 18/1 and then to Mimosa Yellow, Plate 602/1 over basal quarter of petal.

This description was made from a rose that was open for three days in a greenhouse during the month of September at West Grove, Pennsylvania, U.S.A.:

*Color.*—Outer petal: Outside surface—Rose Opal, Plate 022, with base of petal and point of attachment Mimosa Yellow, Plate 602/3. Inside surface: Delft Rose, Plate 020, with point of attachment and area surrounding it Mimosa Yellow, Plate 602/3. Inner petal: Outside surface—Rose Opal, Plate 022 at outer margin, becoming Delft Rose, Plate 020, with point of attachment and area surrounding it Mimosa Yellow, Plate 602. Inside surface—Blood Red, Plate 820/1 at outer margin, becoming Delft Rose, Plate 020, with point of attachment and area surrounding it Mimosa Yellow, Plate 602.

*General color effect.*—Newly opened flower—Geranium Lake, Plate 20, with a broad area of Mimosa Yellow, Plate 602/3 surrounding the point of attachment. 3-days open—Near Delft Rose, Plate 020, but with color slightly more intense.

*Behavior.*—Drop off cleanly.

*Flower longevity.*—On bush in garden—5 days in September. Cut roses grown outdoors and kept at living room temperatures—4 days in September.

*Reproductive organs*

Stamens: Medium number; arranged regularly about pistils; mixed with petaloids.

Filaments: Many; short; most with anthers. Color—Yellow.

Anthers: Open at various times; occasionally an anther fused with a petaloid. Color—Mimosa Yellow, Plate 602.

Pollen: Moderate. Color—Gold.

Pistils: Few.

Styles: Uneven; very short; thin; bunched.

Stigma: Color—White.

Ovaries: Some protruding from receptacle.

Hips: None observed.

Sepals: Permanent; short; spear-shaped.

Seeds: None observed.

*Plant*

Foliage:

*Leaves.*—Compound of 5–7 leaflets; normal abundance; small; moderately leathery.

*Leaflets.*—Oval shaped. Apex—acute. Base—obtuse. Margin—simply serrate.

*Color.*—Mature: Upper surface—Spinach Green, Plate 0960. Undersurface—Lavender Green, Plate 000761. Young: Upper surface—near Scheeles Green, Plate 860. Under surface—Near Spinach Green, Plate 0960/2.

*Rachis (the supporting stem of the compound leaf).*—Light caliper. Upper side—grooved; hairy. Under side—sparsely prickly.

*Stipules.*—Short; narrow; with very short points turning out at an angle of 45°.

*Disease resistance.*—Comparable to that of the average variety grown under the same cultural conditions at West Grove, Pennsylvania, U.S.A.

Growth:

*Habit.*—Dwarf; much-branched.

*Growth.*—Moderate.

*Canes.*—Light.

*Main stems.*—Bright. Color—Spinach Green, Plate 0960. Prickles—several; color: brown. Hairs—none.

*Branches.*—Bright. Color—Spinach Green, Plate 0960. Prickles—several; color: brown, with points greenish. Hairs—none.

*New shoots.*—Dull. Color—Scheeles Green, Plate 860/1. Prickles—several; color: Reddish, overlying Green. Hairs—none.

I claim:

A new and distinct variety of rose plant of the miniature class, substantially as herein shown and described, characterized particularly as to novelty by the unique combination of a somewhat greater than average plant vigor than that of the average miniature rose variety, small flower size, but good flower form, good petal count of the double flowers, and a distinctive and attractive Orange-Scarlet general color tonality of the flowers.

No references cited.

ABRAHAM G. STONE, *Primary Examiner.*